United States Patent
Havenga et al.

(10) Patent No.: US 11,202,634 B2
(45) Date of Patent: Dec. 21, 2021

(54) INSTRUMENT FOR PERFORMING ANASTOMOSIS

(71) Applicants: Implican B.V., Heerenveen (NL); Rijksuniversiteit Groningen, Groningen (NL); Academisch Ziekenhuis Groningen, Groningen (NL)

(72) Inventors: Klaas Havenga, Haren (NL); Jan Nieuwenhuis, Groningen (NL); Olf Boesjes, Blijham (NL)

(73) Assignees: Implican B.V., Heerenveen (NL); Rijksuniversiteit Groningen, Groningen (NL); Academisch Ziekenhuis Groningen, Groningen (NL)

( * ) Notice: Subject to any disclaimer, the term of this patent is extended or adjusted under 35 U.S.C. 154(b) by 233 days.

(21) Appl. No.: 16/466,280

(22) PCT Filed: Dec. 4, 2017

(86) PCT No.: PCT/NL2017/050810
§ 371 (c)(1),
(2) Date: Jun. 3, 2019

(87) PCT Pub. No.: WO2018/101832
PCT Pub. Date: Jun. 7, 2018

(65) Prior Publication Data
US 2020/0078020 A1    Mar. 12, 2020

(30) Foreign Application Priority Data
Dec. 2, 2016 (NL) ............................ 2017917

(51) Int. Cl.
*A61B 17/11* (2006.01)
*A61B 17/072* (2006.01)
(Continued)

(52) U.S. Cl.
CPC .... *A61B 17/1114* (2013.01); *A61B 17/07292* (2013.01); *A61B 17/1155* (2013.01);
(Continued)

(58) Field of Classification Search
CPC . A61B 17/115; A61B 17/11; A61B 17/07292; A61B 17/1114; A61B 17/1155;
(Continued)

(56) References Cited

U.S. PATENT DOCUMENTS

| 4,700,703 A | 10/1987 | Resnick et al. |
| 8,770,460 B2 | 7/2014 | Belzer |

(Continued)

FOREIGN PATENT DOCUMENTS

| DE | 10 2011 055 236 A1 | 5/2013 |
| EP | 2 258 282 A2 | 12/2010 |

(Continued)

OTHER PUBLICATIONS

International Search Report issued in PCT/NL2017/050810; dated Mar. 21, 2018.
(Continued)

*Primary Examiner* — George J Ulsh
(74) *Attorney, Agent, or Firm* — Studebaker & Brackett PC

(57) ABSTRACT

The invention is directed to a method and a surgical instrument, typically a surgical stapler that is configured for performing anastomosis of a first gastro-intestinal tract section to a second gastro-intestinal tract section, both gastro-intestinal tract sections comprising a superficial layer and an intermediate layer. Said method comprises contacting the superficial layers of said gastro-intestinal tract sections and compressing the contacted sections between a first pressure area and a second pressure area, wherein the sum of the first pressure area and the second pressure increases (Continued)

during the compression such that the superficial layers are pressed aside and the intermediate layers are contacted.

15 Claims, 11 Drawing Sheets

(51) Int. Cl.
*A61B 17/115* (2006.01)
*A61B 17/00* (2006.01)

(52) U.S. Cl.
CPC ............ *A61B 2017/00898* (2013.01); *A61B 2017/00951* (2013.01); *A61B 2017/1132* (2013.01)

(58) Field of Classification Search
CPC .......... A61B 2017/00884; A61B 2017/00898; A61B 2017/00951; A61B 2017/1132; A61L 31/145; A61L 31/16
See application file for complete search history.

(56) References Cited

U.S. PATENT DOCUMENTS

| | | |
|---|---|---|
| 2010/0270356 A1 | 10/2010 | Holsten et al. |
| 2014/0309634 A1 | 10/2014 | Weisshaupt et al. |
| 2018/0036063 A1 | 2/2018 | Weisshaupt et al. |

FOREIGN PATENT DOCUMENTS

| | | |
|---|---|---|
| EP | 2 272 442 A1 | 1/2011 |
| EP | 2 620 104 A2 | 7/2013 |
| JP | S50-039086 U | 4/1975 |
| JP | 2009-515569 A | 4/2009 |
| JP | 2013-154187 A | 8/2013 |
| JP | 2013-223765 A | 10/2013 |
| JP | 2014-193329 A | 10/2014 |
| WO | 2009/096822 A1 | 8/2009 |

OTHER PUBLICATIONS

Yasuda (Japanese Patent Office) Notice of Reasons for Refusal in counterpart foreign application JP 2019-529197 dated Oct. 5, 2021, all pages.

Fig. 7A
Fig. 7B
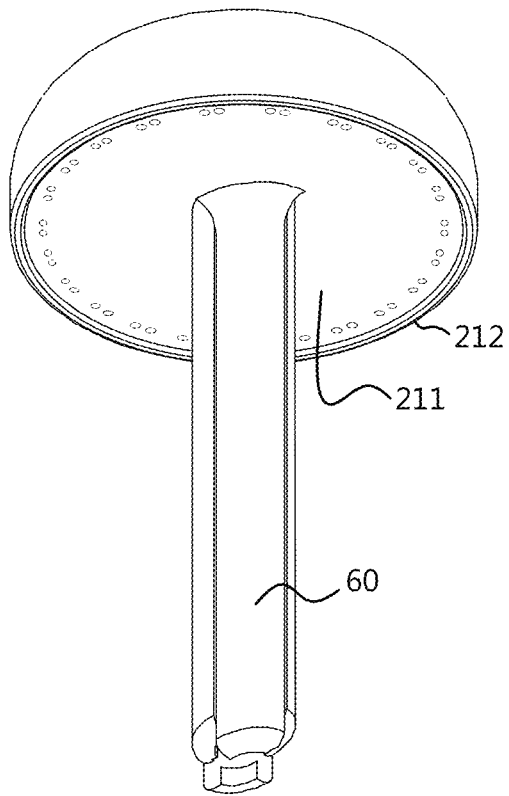
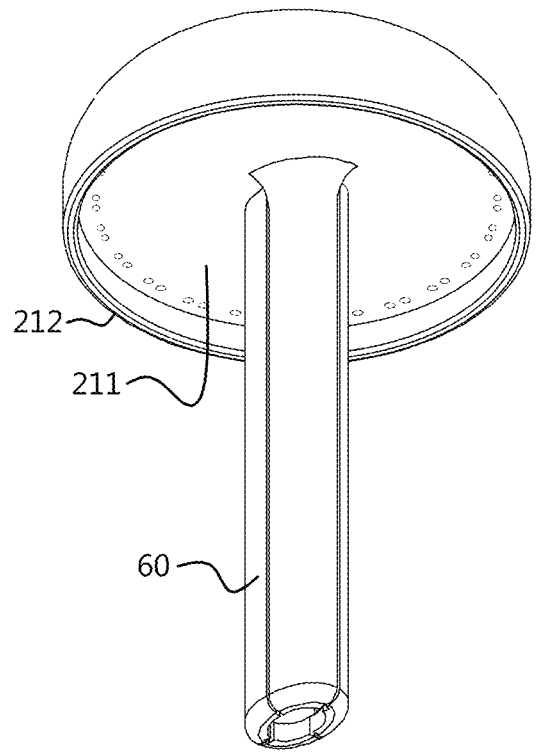

Fig. 8A
Fig. 8B
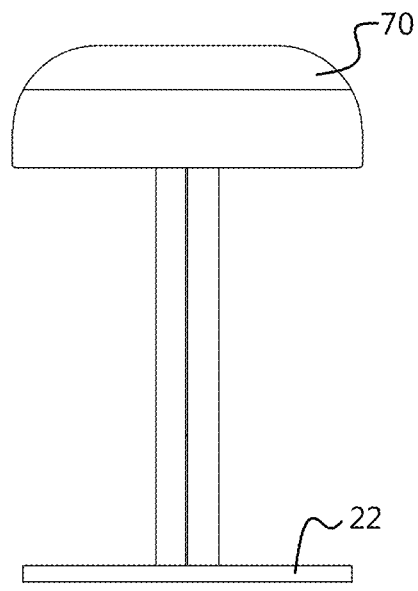
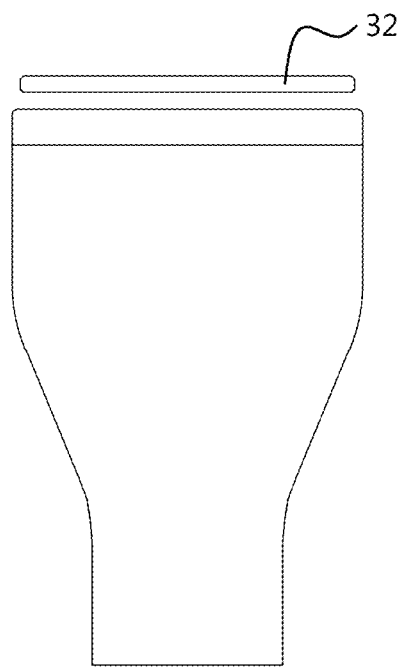
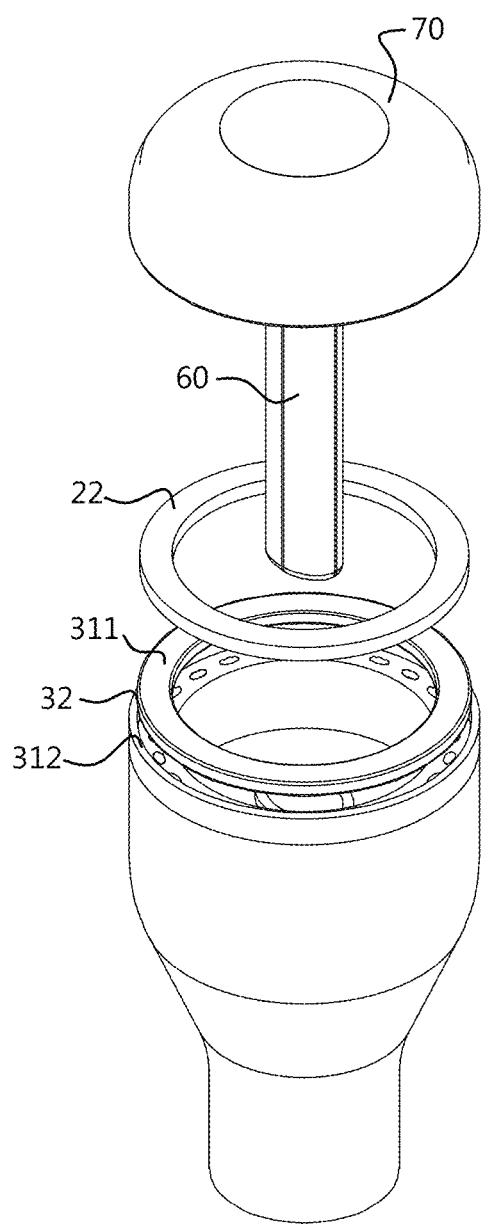

Fig. 9A
Fig. 9B
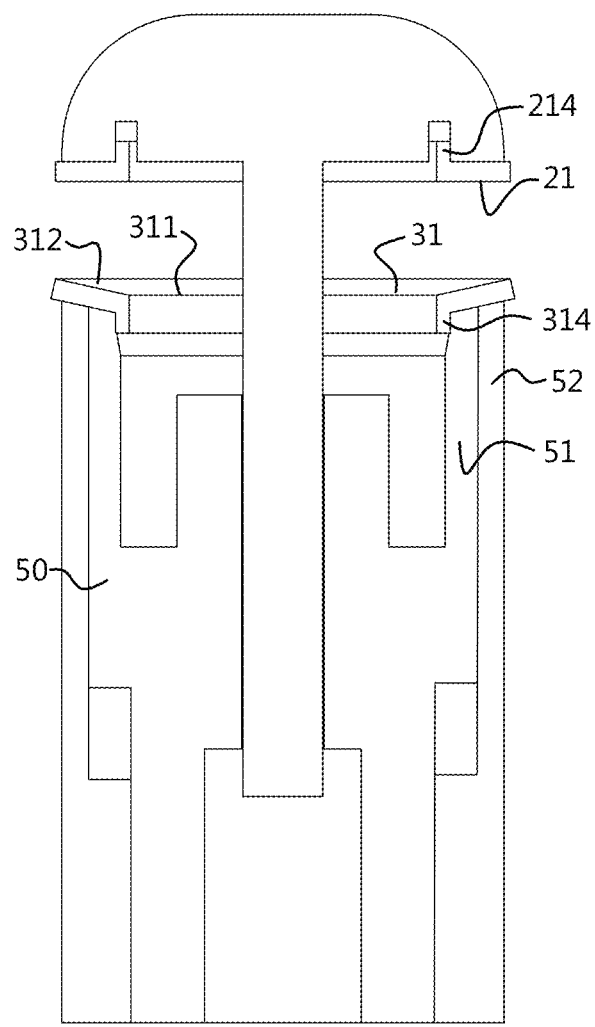
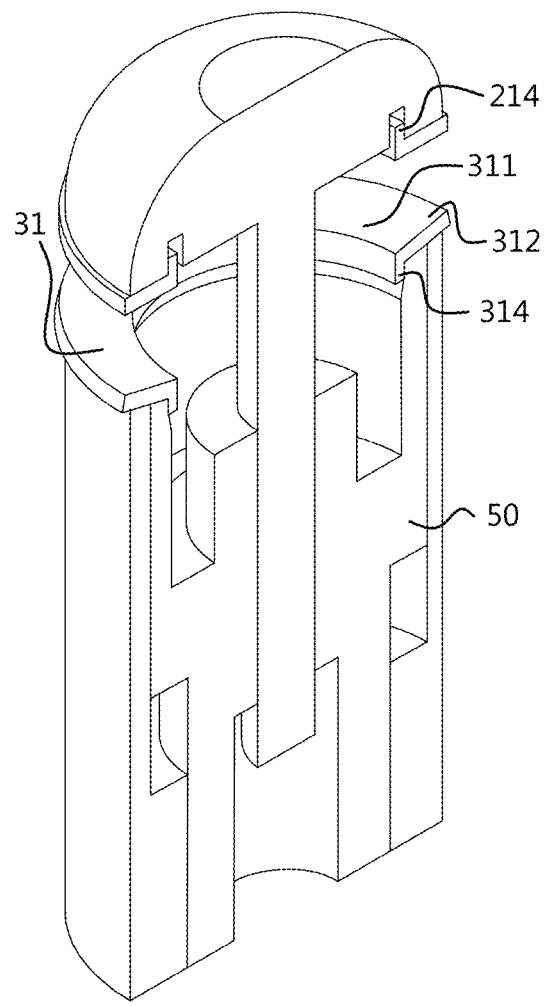

Fig. 12A
Fig. 12B
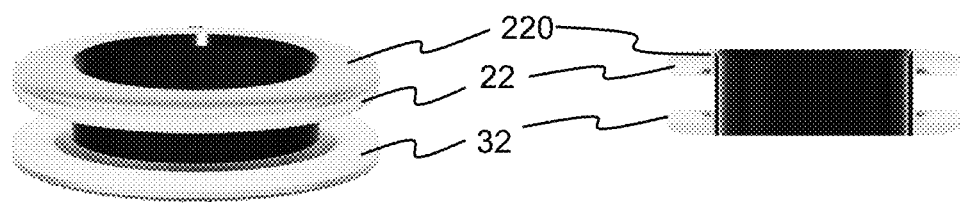
Fig. 13
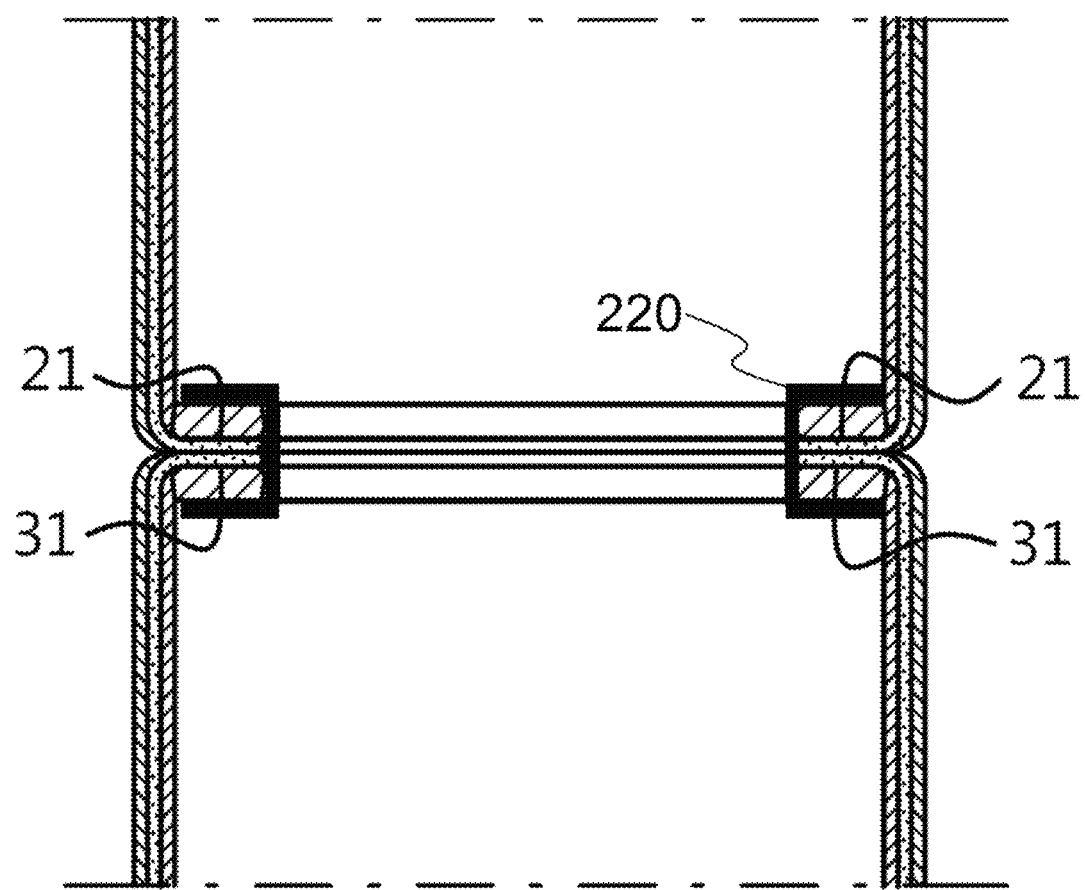

INSTRUMENT FOR PERFORMING ANASTOMOSIS

The invention is directed to a surgical instrument and a method for connecting and fixating bodily tissues. In particular, the present invention is directed to a surgical instrument for performing anastomosis of the gastro-intestinal tract.

Anastomoses, i.e. the joining of two sections of tubular organ sections of the gastro-intestinal tract such as the esophagus, colon or other parts, are frequently associated with complications such a leakage, infections, fibrosis and the like. For instance, anastomotic leakage is observed in about 10% of low anterior resection cases involving anastomosis of the colorectal segment by conventional circular staplers.

Favorable results in terms of preventing complications after anastomosis have been obtained by using compression anastomosis (see e.g. Kaider-Person et al., *The American Journal of Surgery* (2008) 195, 818-826). Conventional compression anastomosis includes for instance clamping and fixating the two tissue layers of the gastro-intestinal tract between two members of a clamping device such as the known Murphy button, Boerema knot, Valtrac™ or magnetic rings (see Cossu et al., *The American Surgeon* (2000) (8), 759-762 and Jansen et al. *Surgery, Gynecoloy & Obstetrics* (1981) 153, 537-545 respectively).

In spite of the favorable results, compression anastomosis is still posed by challenges and therefore the use of conventional surgical staplers is generally standard in anastomosis procedures. Conventional surgical staplers give no compression on the connected bowel segments and preserve the circulation of blood between the staples. It is accordingly desirable to further improve compression anastomosis so it will i.a. become easier to perform and more accessible. It is desired to improve compression anastomosis in terms of the healing process such to reduce post-operational complication.

The tissue of the gastro-intestinal tract is a tubular layered structure basically comprising three layers of different tissue types. The peripheral layer primarily comprises muscularis, the subsequent submucosal layer primarily comprises collagen and the luminal layer primarily comprises mucosa. The present inventors realized that optimal conditions for wound healing of the anastomosis involves contacting and fixating the submucosal layers of the gastro-intestinal tract sections that are to be connected thereby allowing the tissue to heal by primary intent. Healing by primary intent may increase the healing process rate and reduce the risk of leakage, infections, fibrosis and the like.

In order to contact the submucosal layers of the gastro-intestinal tract sections, the submucosal layers of the gastro-intestinal tract sections that are to be connected are preferably stripped from the adjacent muscularis and/or mucosal layers. The present inventors surprisingly realized that this may be achieved by placing a part of the two gastro-intestinal tract sections that are to be connected on top of each other and by then compressing the two gastro-intestinal tract sections between a pressure area to crush the muscularis and/or mucosal layers, followed by increasing said pressure area such that the muscularisis and/or mucosal layers are pressed aside and the submucosal layers are concomitantly stripped from the muscularis and/or mucosal layers and both submucosal layers contact each other.

Accordingly, the present invention provides a method and a surgical instrument for performing anastomosis of a first gastro-intestinal tract section to a second gastro-intestinal tract section, both gastro-intestinal tract sections comprising two superficial layers (e.g. a muscularis layer and a mucosal layer) and an intermediate layer (e.g. a submucosal layer). Said method comprises contacting the respective superficial (muscularis) layers of said gastro-intestinal tract sections and compressing the contacted sections between a first pressure area and a second pressure area, wherein the sum of the first pressure area and the second pressure increases during the compression such that the superficial layers are pressed aside and the intermediate layers are contacted.

The present invention further provides a surgical instrument, in particular a surgical stapler, said instrument comprising:
 a first body having a first pressure area;
 a second body having a second pressure area;
 a connection means connecting the first body and the second body, said connection means configured to move the first body between an open position away from the second body and a closed position near the second body; wherein the first and second bodies are configured to compress the first gastro-intestinal tract section and the second gastro-intestinal tract section between the first pressure area and the second pressure area, wherein the sum of the first pressure area and the second pressure increases during the compression.

The present inventors surprisingly found that anastomosis methods can be improved by stripping the submucosal layers from the muscularis and/or mucosal layers while the first gastro-intestinal tract section and the second gastro-intestinal tract section are compressed. The method of the present invention enables this compressing and stripping by increasing the sum of the total pressure area during the compression. The compression is thus initiated with a smaller total pressure area compared to the final total pressure area.

BRIEF DESCRIPTIONS OF THE DRAWINGS

FIGS. 7A-7B further illustrate part of a surgical instrument.

FIGS. 8A-8B illustrate particular cross-section (FIG. 8A) and perspective (FIG. 8B) views of a surgical instrument.

FIGS. 9A-9B illustrate particular cross-section (FIG. 9A) and cut-through (FIG. 9B) views of a surgical instrument.

FIGS. 10A-10F illustrate particular steps of a method for operating a surgical instrument.

Figure 11:
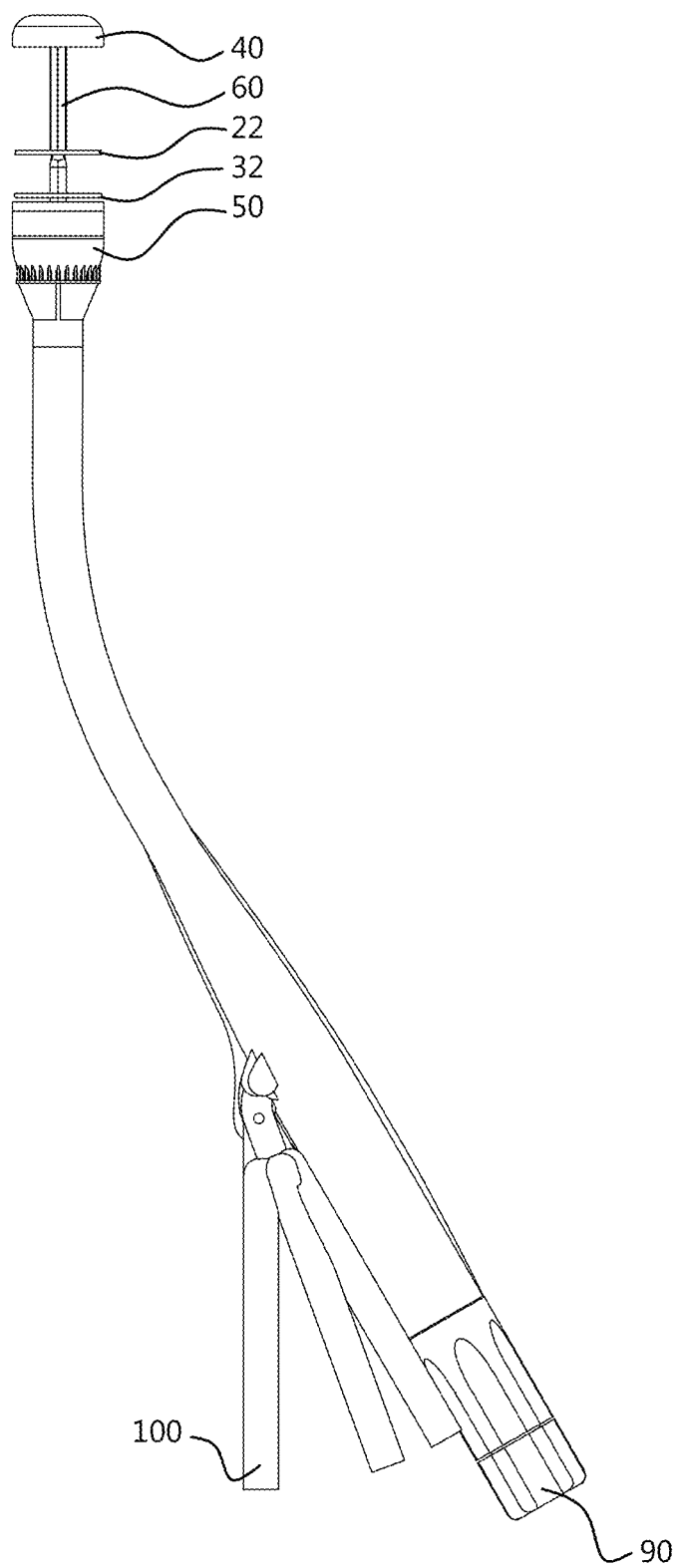

FIG. 11 illustrates a particular embodiment of a surgical instrument.

FIGS. 12A-12B illustrate a preferred part of a surgical instrument.

FIG. 13 illustrates a preferred part of a surgical instrument.

N.B. Although FIGS. 4-11 show a particular surgical circular stapler, the surgical stapler of the present invention is not limited to a surgical circular stapler and may also comprise a surgical linear stapler.

Figure 1A:
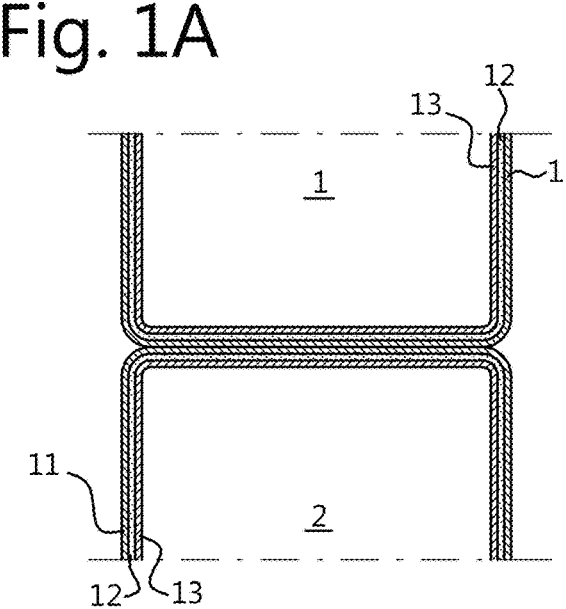
FIGS. 1A-1F illustrate particular steps of a method for operating a surgical instrument.
Figure 1B:
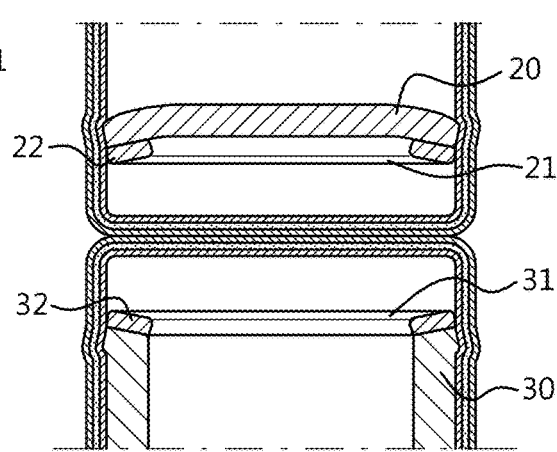
Figure 1C:
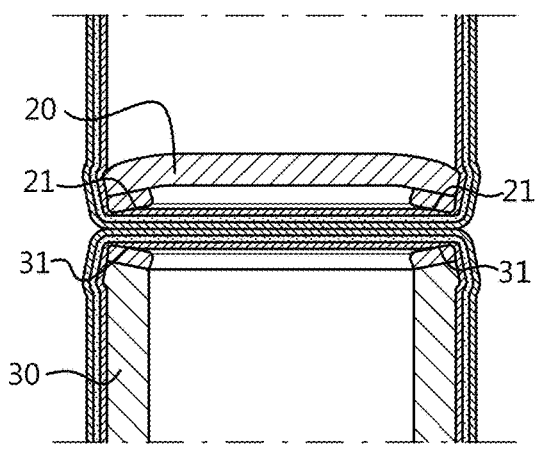
Figure 1D:
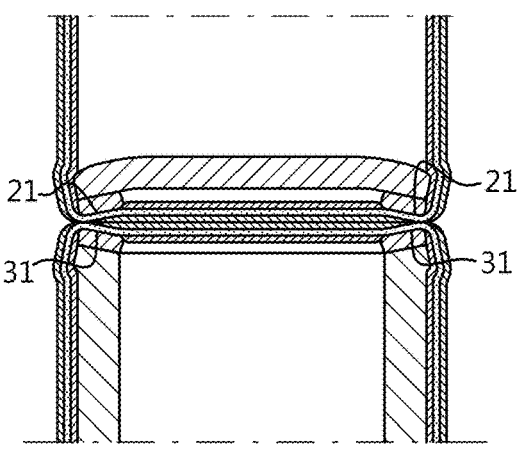
Figure 1E:
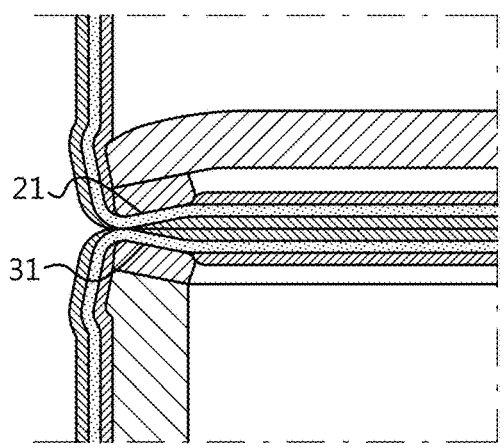
Figure 1F:
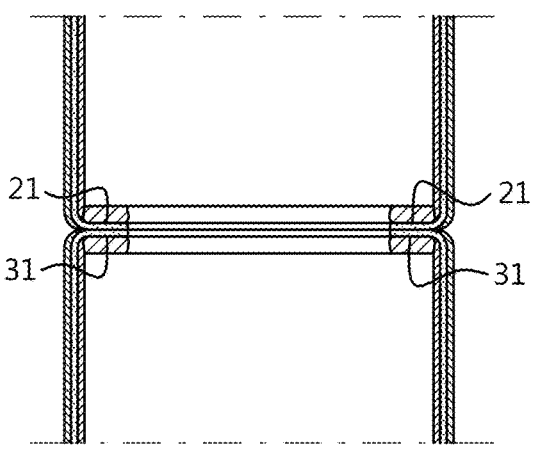

FIG. 1A-F show a schematic illustration of a particular embodiment of the method to operate the surgical instrument of the present invention. FIG. 1A illustrates the first gastro-intestinal tract section and the second gastro-intestinal tract section, each comprising a muscularis layer (11) and a mucosal layer (13) (i.e. the superficial layers) in additional to a submucosal layer (12) (i.e. the intermediate layer). The muscularis layers (11) of each gastro-intestinal tract section are contacted. In FIG. 1B, the first body (20) and second body (30) of the surgical instrument are illustrated being present in the first and second gastro-intestinal tract section, respectively. The first gastro-intestinal tract section and the second gastro-intestinal tract section are compressed in between the first body 20 comprising the first pressure area 21 and the second body 30 comprising the second pressure area 31 (FIG. 1C) during which the sum of the first pressure area and the second pressure area increases during the compression (FIG. 1F illustrates a higher sum of the first pressure area and the second pressure area than FIG. 1E). During compression, the muscularis layers (11) and muscosal layers (13) are pressed aside (FIG. 1D and FIG. 1E) and the submucosal layer 12 are contacted (FIG. 1F). The muscularis layers (11) and muscosal layers (13) may be pressed aside towards the lumen of the gastro-intestinal tract sections (as shown in FIG. 1D and FIG. 1E) or towards the bowel (i.e. outside the gastro-intestinal tract sections, not shown).

A portion of the first and the second gastro-intestinal tract sections can be removed, e.g. by cutting with a knife, such that the internal lumen of the first and second gastro-intestinal tract sections are connected and the anastomosis is complete (FIG. 1F).

In a particular embodiment of the present invention, as for instant illustrated in FIGS. 1A-F, the first pressure area is inclined or slanted with respect to the second pressure area. This results in that the sum of the first pressure area and the second pressure area increases during the compression. In other words, during use, the first pressure area and/or second pressure area are slanted or inclined with respect to the first and second gastro-intestinal tract sections that are compressed.

By contacting the submucosal layers, a watertight seal is provided that i.a. limits bacterial contamination at the site of contact and a healing process by primary intent is promoted.

Figure 2A:
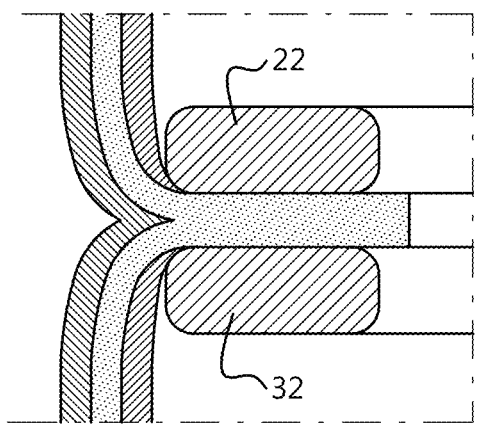
FIGS. 2A-2B illustrate preferred steps of a method for operating a surgical instrument.
Figure 2B:
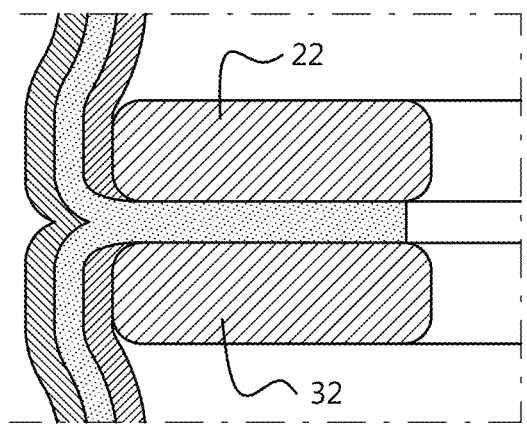

In a preferred embodiment, as illustrated in FIGS. 2A-B, the method to operate the surgical instrument further comprises applying a swellable hydrogel (22, 32) on the part of the compressed first gastro-intestinal tract section and the second gastro-intestinal tract section (FIG. 2A) to be connected and sealed, fixating said swellable hydrogel onto at least part of the contacted gastro-intestinal tract section and allowing the hydrogel to swell so to exert a force on the sealed gastro-intestinal tract sections (FIG. 2B). The hydrogel may swell due to the absorption of water or other fluids and this swelling, of for instance about 150 vol %, may results in additional submucosa being contacted (cf. FIGS. 2A and 2B) without compromising vascularization of these additionally contacted submucosal layers 11. Sufficient vascularization of the bowel layers promotes the healing process.

The additional contact of the respective submucosal layers of the first and second gastro-intestinal tract sections as for instance shown in FIGS. 2A and 2B, can typically be achieved by providing the hydrogel in two rings which each have an outer diameter that approximate the inner diameter of the first and second gastro-intestinal tract sections in which the two rings are to be placed. The swelling of the hydrogel results in the exertion of an outwardly directed force which result in additional inter-submucosal contact.

The swellable hydrogel may comprise known hydrogel such as swellable polyurethanes and the like. The swellable hydrogel is typically capable of absorbing moisture to swell in an amount of 0-100 vol %, preferably 10-80 vol %, more preferably about 50 vol % with respect to the original volume of the hydrogel. Swelling of the hydrogel after it has been placed on the layers to be sealed improve the sealing and healing process.

Swellable hydrogels are known for medical applications. Cale, and Khutoryanskiy, European Polymer Journal 65 (2015) 252-267 discloses hydrogel of which some are capable of swelling, for instance the hydrogels disclosed in EP0524718. Additional suitable hydrogels for this purpose may comprise e.g. polyethylene glycol and polybutylene terephthalate multiblock copolymer such as commercially available under the tradename PolyActive™ and disclosed by Bos et al., Pharmaceutical Technology October 2001 p. 110-120, or thermoplastic polyurethanes based on aliphatic hydrophilic polyether such as commercially available under the tradename Tecophilic™ and disclosed by Verstraete et al., International Journal of Pharmaceutics 2016, 15, 214-221.

Figure 3:
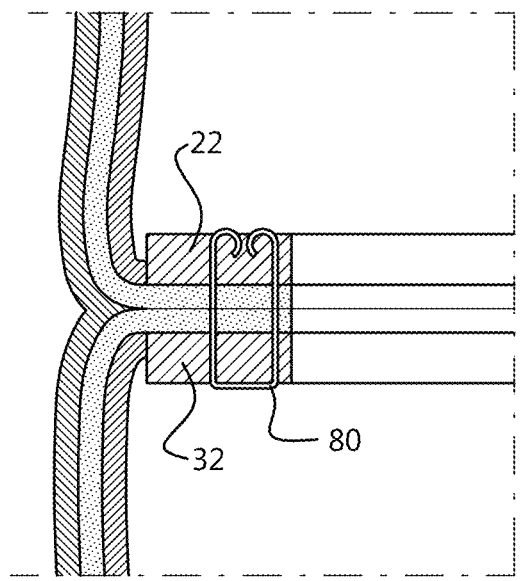
FIG. 3 illustrates part of a surgical instrument.

In FIG. 3, a particular embodiment of the hydogel 22,32 is schematically illustrated wherein the hydrogel 22,32 is fixated by staples 80.

Suitable means for fixation of the hydrogel and thus the first and second gastro-intestinal tract sections comprise staples sutures, glue and/or rivets.

In FIGS. 4A-F, a particularly preferred embodiment of the present invention is illustrated, wherein the first gastro-intestinal tract section and the second gastro-intestinal tract section are compressed by using a surgical stapler comprising an anvil (40) comprising the first pressure area 21 and a casing 50 comprising the second pressure area 32. The surgical stapler is generally applied in an open position (FIG. 4A) in the lumen of the gastro-intestinal tract, wherein the anvil 20 is placed in the first gastro-intestinal tract section (e.g. the proximal part of the bowel) and the casing 30 is placed in the second gastro-intestinal tract section (e.g. the distal part of the bowel).

The hydrogel 22,32 may also be provided on the surgical stapler.

Figure 4A:
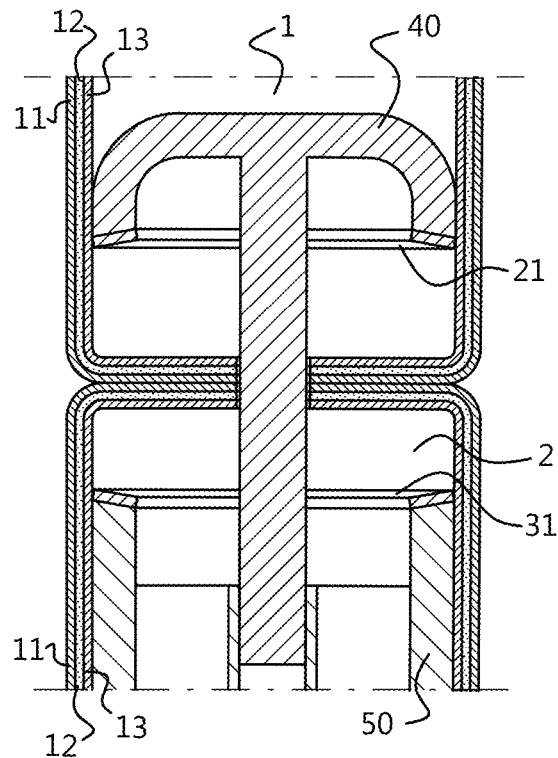
FIGS. 4A-4F illustrate particular steps of a method for operating a surgical instrument.
Figure 4B:
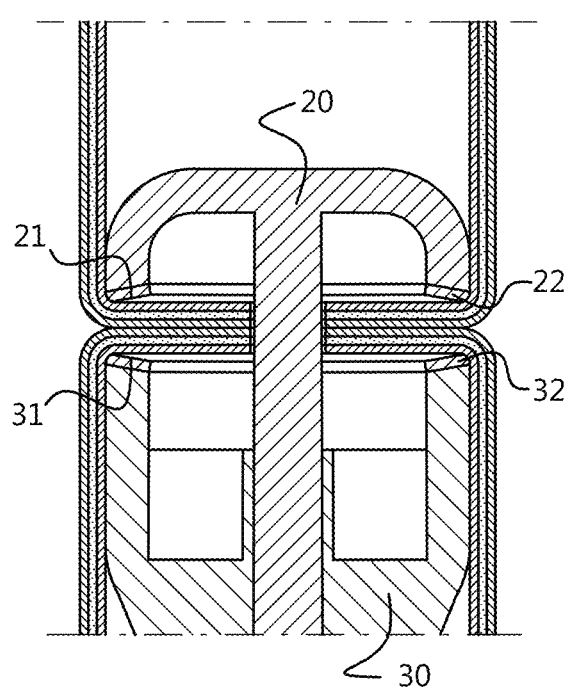
Figure 4C:
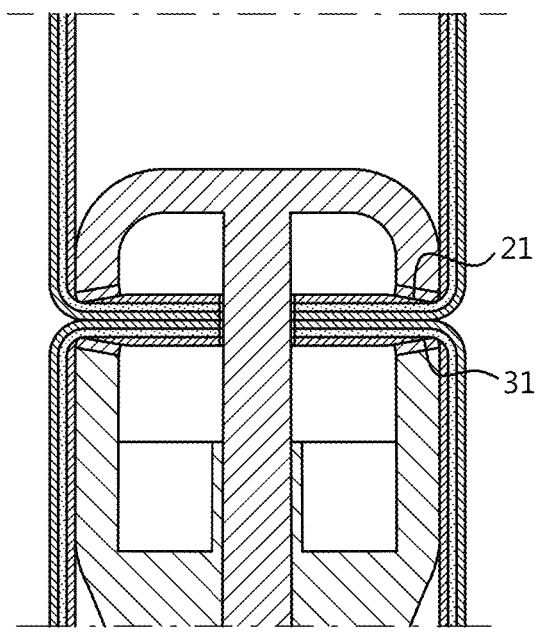
Figure 4D:
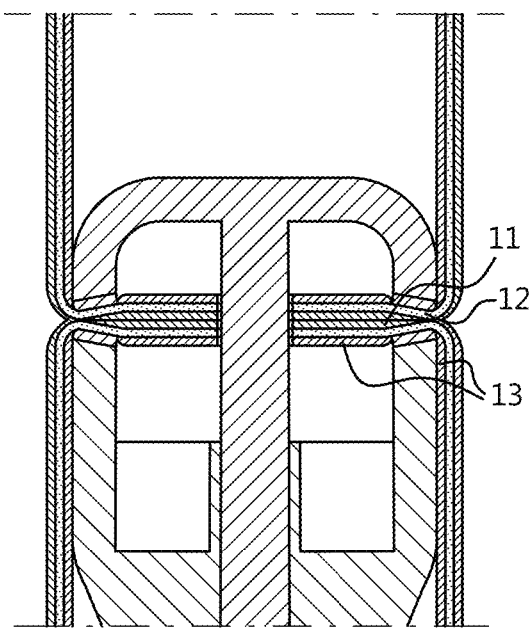

During use of the surgical stapler, the first body is moved from the open position way from the second body, towards a closed position near the second body (FIG. 4B) such that the compression of the first gastro-intestinal tract section and the second gastro-intestinal tract section may commence (FIG. 4C). The sum of the first pressure area and the second pressure area increases during the compression (cf. FIGS. 4B-E). In FIG. 4B, the sum of the first pressure area and the second pressure area comprises the initial points of contact of the slanted first pressure area and the second pressure area. In FIG. 4F, the sum of the first pressure area and the second pressure area is larger than that sum in FIG. 4B.

Figure 4E:
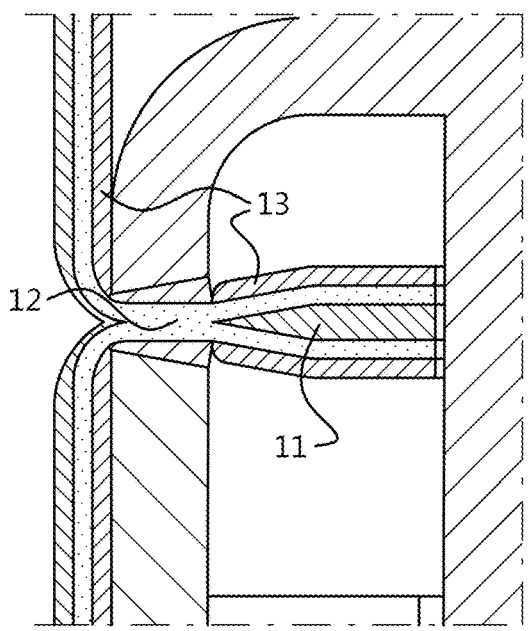
Figure 4F:
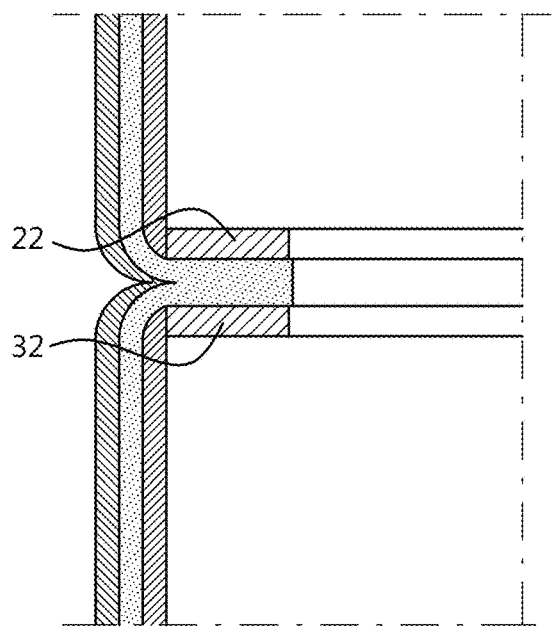

During compression the superficial layers (e.g. muscularis layers (11) and muscosa layers (13)) are pressed aside and the intermediate layers are contacted (FIG. 4D) up to a point wherein a substantially watertight sealing between the intermediate layers (e.g. submucosal layers 12) is obtained (FIG. 4E).

After the compression by the surgical stapler is completed, a section of the first gastro-intestinal tract section and the second gastro-intestinal tract section can be removed, e.g. by cutting with a knife that is provided in the stapler (not shown), such that the lumen of the first gastro-intestinal tract section and the second gastro-intestinal tract section are connected (FIG. 4F). This cutting with a knife is also common for conventional circular staplers.

Preferably, the sum of the first pressure area and the second pressure area increases in the direction of the nearest cutting section of the tubular section, i.e. in the direction of the nearest part of the knife during cutting, e.g. in the direction of the center of the cross-section of the stapler in case the stapler is a circular stapler (i.e. towards the lumen of the bowel). This prevents the accumulation of debris, bacteria and other undesired matter ending up near the wound that will have to heal at the periphery of the pressure areas (site of contact of the submucosal layers of the connected gastro-intestinal tract sections) since this debris, bacteria and the like are pushed towards the lumen of the bowel which continuity is restored. Since, the lumen of the bowel generally comprises many bacteria and debris, it is less harmful to push the debris and bacteria towards and into the lumen than in the direction of the outside of the bowel (i.e. into the abdominal cavity).

A particular advantage of the present invention is that the swellable hydrogel may be placed and fixated on the contacting intermediate layers (e.g. by staples or other means for fixation) and that swelling of the swellable hydrogel may further press aside the mucosa and musculari, without compromising vascularization, thereby facilitating the water tightness of the submucosa connection and healing by primary intent.

The means for fixation and the swellable hydrogel are typically released from the patient's body by necrosis of the submucosa.

In a preferred embodiment, the first body and/or second body of the surgical instrument comprise a swellable hydrogel. The swellable hydrogel may be positioned on the first and/or second body such that during uses, the first gastro-intestinal tract section and the second gastro-intestinal tract section can at least partially be compressed between the swellable hydrogel.

In the case that the swellable hydrogel is present, at least part of the swellable hydrogel surface area is part of the first and/or second pressure area in between which the gastro-intestinal tract sections are compressed. In a particular embodiment, the total pressure area may entirely be comprised by the swellable hydrogel. In another embodiment, the swellable hydrogel may provide only part of the total pressure area in between which the gastro-intestinal tract sections are compressed.

The swellable hydrogel may for instance be fixated by fixation means to the first and/or second body. Examples of such means include for instance pins that protrude from the first and/or second body into the swellable hydrogel. Additionally or alternative, the hydrogel and/or the first and/or second body may also comprises adhesive properties such that the hydrogel loosely adheres to the first and/or second body. The fixation of the swellable hydrogel to the first and/or second body may be releasable or non-releasable.

A non-releasable fixation, which may be preferred, may for instance be achieved by fixating the hydrogel at a section which is removed together with part of the section of the first gastro-intestinal tract section and the second gastro-intestinal tract section which can be removed, e.g. by cutting with a knife (vide supra). In other words, the hydrogel is also cut by the knife and the part that is fixated to the the first and/or second body can be removed together with the the first and/or second body and the sections of the first and second gastro-intestinal tract section that are to be removed.

For instance, in a particular embodiment, wherein the surgical stapler is a circular surgical stapler and the hydrogel is comprised in one or two rings (vide infra), and wherein the circular surgical stapler comprises a circular knife, the inner diameter of the hydrogel-comprising ring may be smaller than the diameter of the circular knife such that after the hydrogel has been fixated by the means for fixation of the hydrogel (e.g. staples and/or rivets). The circular surgical stapler may further be configured such that the knife can create a cut to separate the part of the hydrogel-comprising ring that is fixated to the circular surgical stapler and the part of the hydrogel-comprising ring that has been fixated to the gastro-intestinal tract sections. The cut may also be created before the hydrogel-comprising ring that has been fixated to the gastro-intestinal tract sections by maintaining the position ring in between the anvil and the casing of the surgical stapler.

Conventional surgical instruments such as surgical staplers are known under the tradenames Endopath™ and DST Series™ EEA™ Staplers, by Ethicon and Medtronic respectively, and for instance disclosed in US2005059996 and U.S. Pat. No. 6,503,257, both which are incorporated herein. The conventional staplers are not capable of contacting the submucosal layers of the bowel. The conventional staplers are typical configured such that during operation and stapling, as small distance (of about 1.5 to 2 mm) remains in between the anvil and stapler casing. This results in a conventionally stapled anastomosis that heals via secundam (secondary intent).

The surgical instrument of the present invention enables contacting of the submucosal layers and providing a watertight sealing between the contacted submucosal layers. This enable healing of the anastomosis wound via a primary healing process. The first and second bodies of the present surgical instrument are shaped or configured in such a manner that the total pressure area in between which the gastro-intestinal tract sections on which anastomosis is performed are compressed (i.e. sum of the first pressure area and the second pressure area), increases during the compression. By providing such a shape that the compression commences with a relatively small total pressure area, the superficial layers (i.e. muscularis layers and muscosa layers) that cover the intermediate layers are compressed and pushed away. During further compression, these superficial layers are pushed even further away due to the increasing total pressure area. The total area of the exposed submucosal layers thus increases and is allowed to be contacted and fixated as such.

In a particular embodiment, the first and/or second body are configured such that during use, the first gastro-intestinal tract section and the second gastro-intestinal tract section are initially compressed between an inclined first pressure area and/or inclined second pressure area (e.g. as shown in FIGS. 4A-F and 10A-F).

In a particularly preferred embodiment the surgical instrument comprises a surgical stapler wherein the first body comprises an anvil and the second body comprises a casing that comprises a staple cartridge and a stapler base through which staples can be driven against the anvil.

Figure 5A:
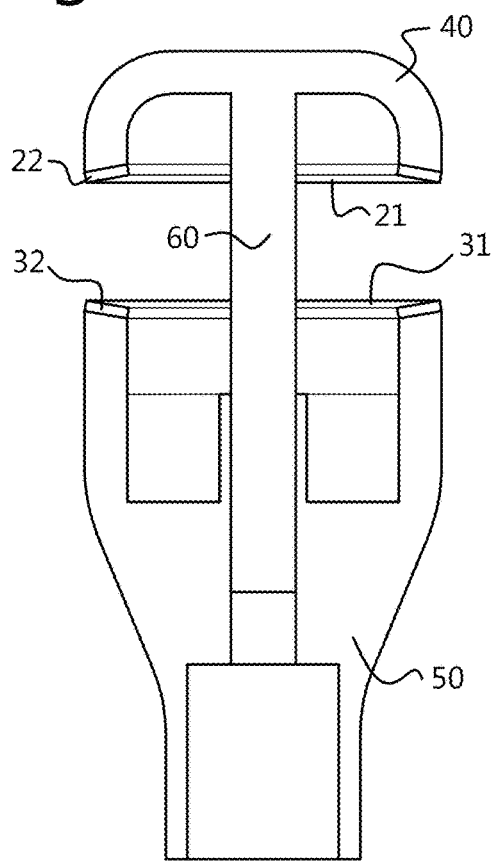
FIGS. 5A-5B illustrate particular cross-section (FIG. 5A) and cut-through (FIG. 5B) views of a surgical instrument.
Figure 5B:
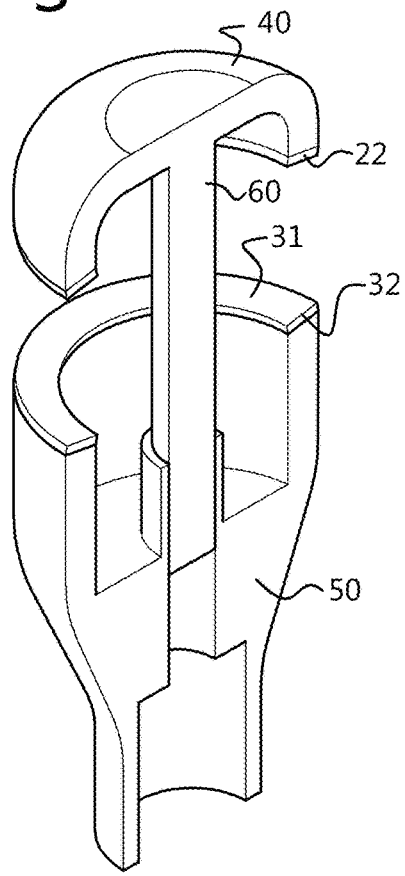
Figure 6A:
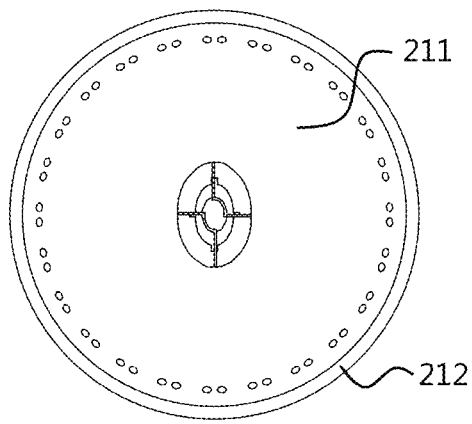
FIGS. 6A-6D illustrate part of a surgical instrument.
Figure 6B:
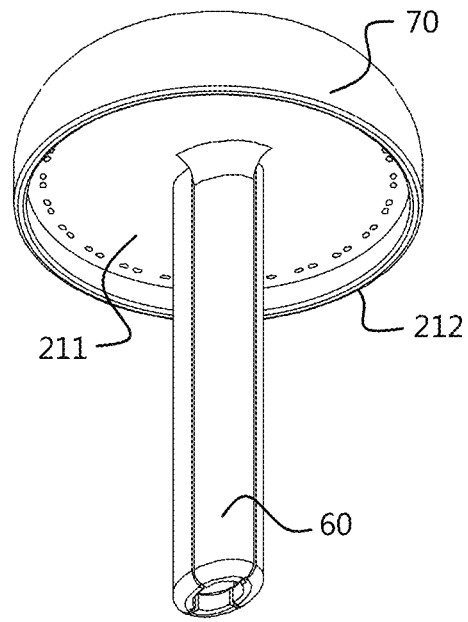
Figure 6C:
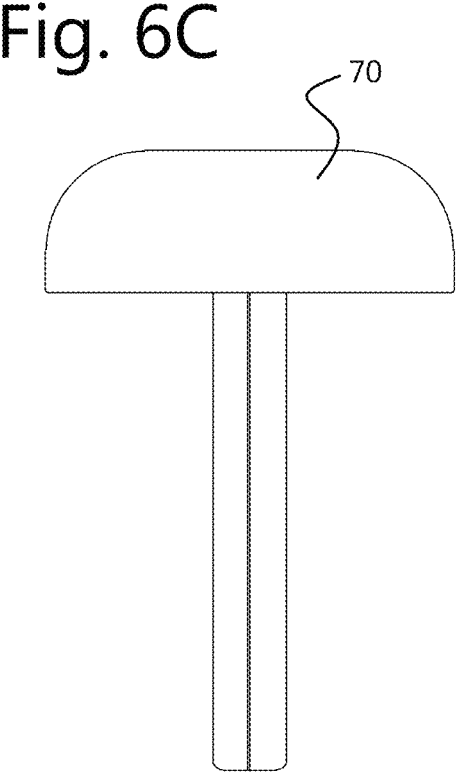
Figure 6D:
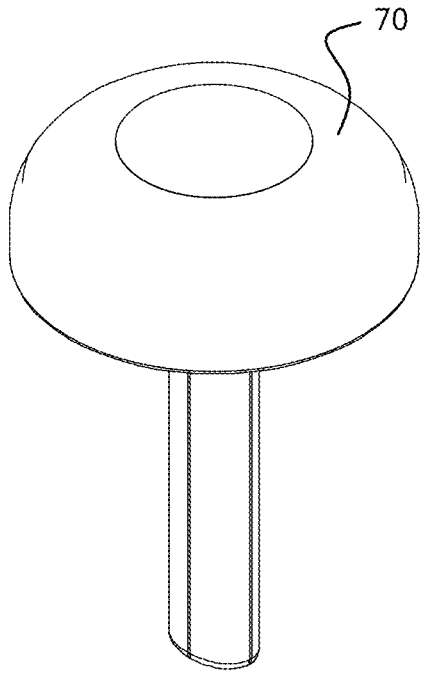
Figure 10A:
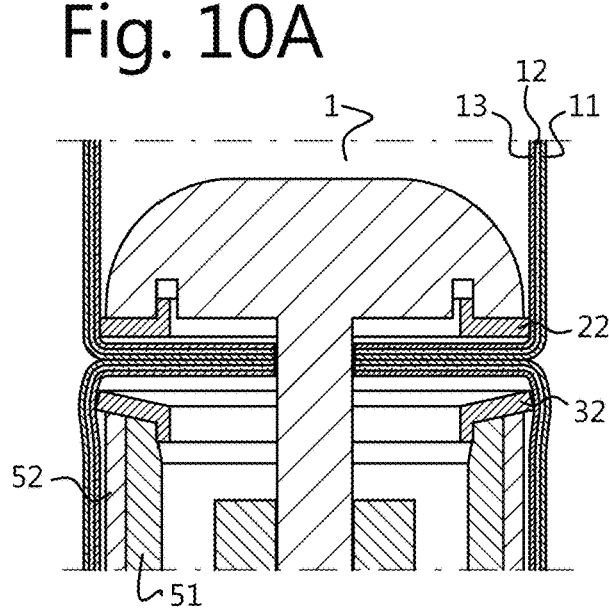
Figure 10B:
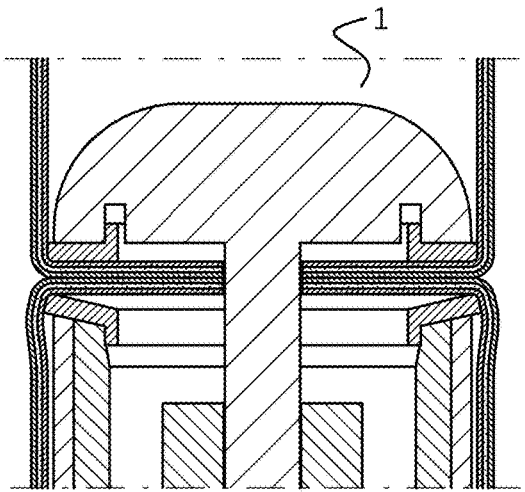
Figure 10C:
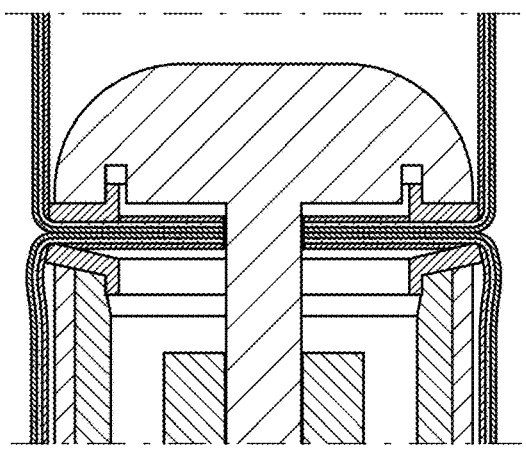
Figure 10D:
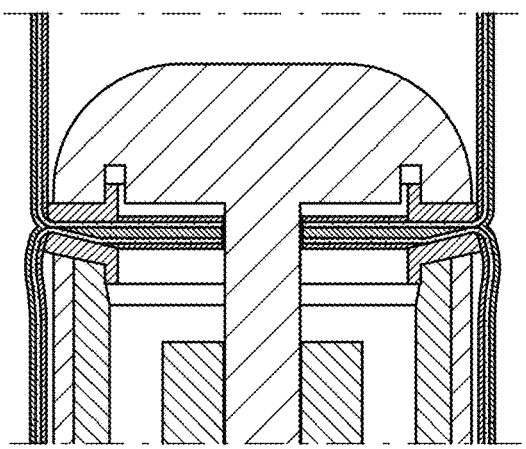
Figure 10E:
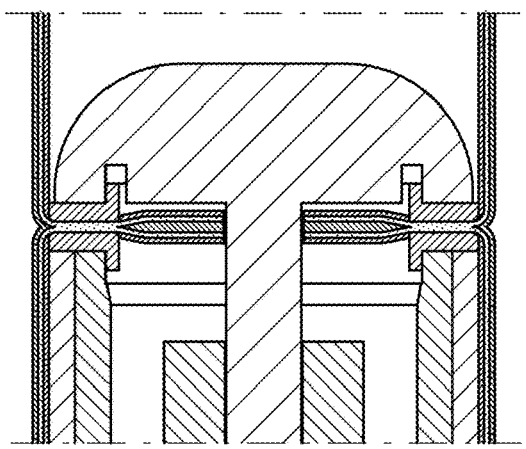
Figure 10F:
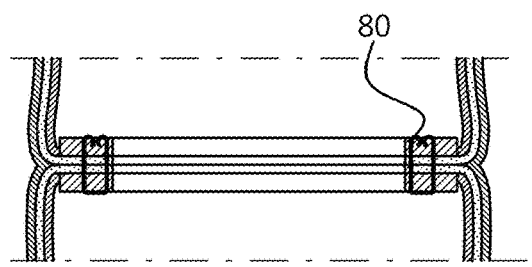

FIGS. 5A and 5B illustrates a cross-section (5A) and a cut-through (5B) a particular embodiment of the surgical stapler in accordance with the present invention. The anvil 40 comprising the first pressure area 21 is connected by the connecting means 60 (e.g. a telescopic shaft comprising screw thread) to the casing 50 that comprises the second pressure area 31. The parts of the anvil and the casing comprising respectively the first and second pressure areas may comprise swellable hydrogel 22, 32.

The present surgical stapler can be operated as described herein-above and illustrated in FIG. 4A-F. The hydrogel is typically resistibly compressible to a certain extent, such that the intermediate (submucosa) layers can be contacted and fixated over the entire sum of the first and second pressure area (cf. FIGS. 4D and 4F) such that an optimal sealing is obtained.

The inventors surprisingly found that leakage of the anastomosis may partially be the result of the microbiome. Without wishing to be bound by theory, certain bacteria (e.g. *Enterococcus faecalis*) are believed to be capable of excreting enzymes capable of dissolving collagen. (see e.g. Van Praagh et al. Surgical Endoscopy (2016) 30, 2259-2265; Shogan et al. Science Translational Medicine (2015) 7, 286ra68) To limit or prevent the proliferation of such bacteria, it may be preferred that the hydrogel comprises one or more antibiotics. Suitable antibiotics may include polymyxin E, tobramycin, amphotericin B, vancomycin and gentamicine. (see e.g. Schardey et al. Annals of Surgery (1997) 225, 172-180; Roos et al. British Journal of Surgery (2013) 100, 1579-1588).

In a preferred embodiment, that is illustrated FIG. 12A-B, the surgical instrument comprises a cover on at least part of the surface of the swellable hydrogel that does not contact the gastro-intestinal sections after application sealing. As such that delivery of the antibiotics is directed to the sealed tissue sections of the tissue of the gastro-intestinal tract and a higher dosage of antibiotics can be delivered. Preferably, entire said surface of the hydrogel is covered by the cover, such that the hydrogel is essentially entirely surrounded by the cover and the gastro-intestinal sections, as illustrated in FIG. 13.

Similar to conventional surgical stapler, the casing 50 may comprise a staple cartridge and a stapler base through which staples can be driven against the anvil. Alternatively or additionally, the casing may comprise rivets cartridge and one or more drivers to drive the rivets through the sealed intermediate layers (submucosa) and the optionally present hydrogel.

In a particular embodiment, the anvil of the comprises surgical stapler an inner anvil part having an inner anvil pressure area and an outer anvil part having an outer anvil pressure area, said inner anvil pressure area and outer anvil pressure area being part of the first pressure area, wherein the inner anvil part is configured to be independently movable from the outer anvil part such that the first gastro-intestinal tract section and the second gastro-intestinal tract section can be compressed first between the outer anvil pressure area and at least part of the second pressure area and subsequently further compressed between the inner anvil pressure area and at least part of the second pressure area.

FIG. 6A-D illustrates part of a particular embodiment of the anvil comprising the inner anvil part comprising the inner anvil pressure area 211 and further the outer anvil part 70 comprising the outer anvil pressure area 212. The rim of the outer anvil part that comprises the outer anvil pressure area 212 is typically about 1 mm in width. The width may vary depending on the desired application of the surgical stapler comprising the anvil.

The inner and outer anvil parts may be connected by connecting means 60, which also connect the anvil to the casing (not shown). In this particular embodiment, the connecting means 60 may be configured such that the inner anvil can slide independently of the outer anvil such that the inner anvil pressure area 211 and the outer anvil pressure area 212 can be joined to form a single pressure area. During operation, the first gastro-intestinal tract section and the second gastro-intestinal tract section are first compressed in between the outer anvil pressure area 212 and the second pressure area (not shown) to press the superficial tissue layers aside and connect the intermediate (submucosa) layers. Subsequently, by sliding the inner anvil part such that the inner anvil pressure area 211 will join the outer anvil pressure area 212, the sum of the first pressure area and the second pressure area will increase, sliding more of the superficial tissue layers aside and enable full contact between the intermediate layers.

FIGS. 7A and 7B is a further illustration of the anvil comprising the inner and outer anvil parts. FIG. 7B shows the connecting means 60 in a sliding position such that the inner anvil pressure area 211 and the outer anvil pressure area 212 are not joined to form a single pressure area. In FIG. 7A, the connecting means 60 in a sliding position such that the inner anvil pressure area 211 and the outer anvil pressure area 212 are joined to form a single pressure area.

In the embodiments wherein the anvil comprises an inner and outer anvil part, the anvil may also further comprise the swellable hydrogel. FIGS. 8A and 8B illustrates part of a particular embodiment of the surgical stapler comprising two rings of the swellable hydrogel. FIG. 8A illustrates the cross-section and FIG. 8B illustrates a perspective view. One ring of the swellable hydrogel 21 falls within the outer anvil part onto the inner anvil part. The other ring of the swellable hydrogel 22 falls within part of the casing that comprises a protruding rim. The ring of the swellable hydrogel 22 comprising pressure area 311 may form the second pressure area together with pressure area 312.

In another particular embodiment the stapler base of the surgical stapler comprises an inner stapler base part having an inner stapler base pressure area and an outer stapler base part having an outer stapler base pressure area, said inner stapler base pressure area and outer stapler base pressure area being part of the second pressure area, wherein the inner stapler base part is configured to be independently movable from the outer stapler base part such that the first gastro-intestinal tract section and the second gastro-intestinal tract section is first compressed between the outer stapler base pressure area and at least part of the first pressure area and subsequently further compressed between the inner stapler base pressure area and at least part of the first pressure area.

FIGS. 9A and 9B illustrates a cross-section (9A) and a cut-through (9B) of a particular embodiment of casing 50 that comprise the stapler base comprising the inner stapler base part 51 and the outer stapler base part 52. For illustration purposes, a particular anvil is also show, but the illustrated stapler base may also be combined with another anvil (e.g. with the anvil comprising the inner anvil part and the outer anvil part as described herein above). In addition, the optionally present hydrogel 31 is illustrated. In case the hydrogel 31 is present, the inner stapler base pressure area 311 and the outer stapler base pressure area 312 may be part of the hydrogel 30. The stapler base may be configured such that the inner stapler base part 51 can slide independently of the outer anvil such that the inner stapler base pressure area 311 and the outer stapler base pressure area 312 can be joined to form a single pressure area.

FIGS. 10A-F illustrate the operation of the particular embodiment of the invention described above wherein the stapler base comprises the inner stapler base part 51 and the outer stapler base part 52. Similar to described herein-above, the stapling instrument may be operated such that the first gastro-intestinal tract section and the second gastro-intestinal tract section having layers 11, 12 and 13 are first compressed in between the first pressure area 21 and the outer stapler base pressure area 312 to press the superficial tissue layers aside and connect the intermediate (submucosa) layers (cf. FIGS. 10A to 10D). Subsequently, by sliding the inner stapler base part such that the inner stapler base pressure area 311 will join the outer stapler pressure area 312, the sum of the first pressure area and the second pressure area will increase, sliding more of the superficial tissue layers aside and enable full contact between the intermediate layers (cf. FIG. 10E). After fixation the hydrogel rings 22 and 32 with for instance staples 80, a knife (not shown) may cut away a doughnut shaped section of the first gastro-intestinal tract section and the second gastro-intestinal tract section such that the fixed tract section remain ((cf. FIG. 10F).

For the embodiments wherein the anvil and/or staple base comprise inner and outers parts, it is preferred that it protrudes from the outer edges of the anvil and/or casing. For instance, in case the surgical instrument is a surgical circular stapler, the outer diameter of the hydrogel rings 21, 31 is preferably larger than the outer diameter of the anvil and/or casing, whichever comprises inner and outers parts. The protrusion of the hydrogel from the edge of the anvil and/or staple base reduces the risk that the hydrogel is pushed inwards by the outer parts upon compression. This greatly increases overall reliability of the instrument and the method of the present invention.

The surgical instrument according to the present invention typically further comprises a knife for creating a cut in a cutting section of the gastro-intestinal tract sections. It is preferred that the first body and/or the second body are further configured such that during use, the sum of the first pressure area and the second pressure area increases in the direction of the nearest cutting section of the tubular gastro-intestinal tract sections, e.g. in the direction of the center of the cross-section of the circular stapler which is the lumen of the bowel. After cutting, part of gastro-intestinal tract section may be removed to connect the lumen of the first and second gastro-intestinal tract sections. By configuring the first and the second body such that the sum of the pressure area increased towards the cutting section, the debris, bacteria and other undesired material will be pushed towards the lumen of the bowel and will thus not interfere at the site of primary wound healing as described herein above. This facilitates healing of the anastomosis wound.

FIG. 11 illustrates a particular embodiment of the surgical circular stapler of the present invention. The surgical circular stapler comprises anvil 40 and casing 50 that are connected by the connecting means 60. The surgical circular stapler may further comprise rings of swellable hydrogel 22,32.

In a preferred embodiment of the surgical circular stapler, one or both of the swellable hydrogel rings comprises a raised edge 224,324 at the inner diameter of the ring (cf. FIGS. 9A, 9B). This raised edge may fixate, e.g. by using an adhesive and/or clamping, the swellable hydrogel ring to the anvil or the casing. After the hydrogel ring is placed on the gastro-intestinal tract section and fixated by e.g. staples, the knife may create a cut in between the raised edge and the outer diameter of the hydrogel ring such that inner part of the hydrogel ring comprising the raised edge can be removed together with the doughnut part of gastro-intestinal tract section that is removed.

The connection means 60 connecting the anvil 40 and the casing 60 is configured to move the anvil between an open position away from the casing and a closed position near the casing. The moving between the open and closing position can for instance be carried out by turning the adjusting means 90. The compression may be carried out by continuation of turning the adjusting means 90 after the anvil is brought to the close position. After the anvil is brought in the desired position relative to the casing, lever 100 may be operated to fixate the contacted gastro-intestinal tract sections.

The surgical stapler of the present invention may be configured such that in the closed position that anvil is at a minimal, predetermined, distance, e.g. about 1.4 mm, from the casing. Typically, submucosal layers of bowel section are slightly thicker than 1.4 mm. Configuring the surgical stapler such that the distance between the anvil and the casing can not be less than a minimal distance (e.g. 1.4 mm) will prevent undesired over-compression of the submucosal layers and cutting or tearing of these layers. However, the thickness of submucosal layers may be different for each patient.

It is preferred that the surgical stapler of the present invention may be adapted such that the force of compression is indicated. The advantage of such a configuration is that excessive compression pressures that may cause the pressure area to crush and destroy the submucosal layers can be avoided.

In a preferred embodiment, the compression of the surgical instrument may be obtained in a staged and revisable manner. Preferable, a partially compressed stapler may be released such that the operating surgeon may reposition the stapler, e.g. to release any tension on one of the gastro-intestinal tracts if necessary.

FIGS. 4-11 illustrate particular embodiments of a surgical circular stapler. However, the surgical stapler of the present invention is not limited to surgical circular staplers and may also comprise surgical linear staplers.

The invention claimed is:

1. A surgical instrument for performing anastomosis of a first gastro-intestinal tract section and a second gastro-intestinal tract section, said instrument comprising:
 a first body having a first pressure area;
 a second body having a second pressure area;
 a knife for creating a cut in a cutting section of said gastro-intestinal tract sections;
 connection means connecting the first body and the second body, wherein the connection means is configured to move the first body between an open position away from the second body and a closed position near the second body;
 wherein the first body and the second body are configured such that, during use, the first gastro-intestinal tract section and the second gastro-intestinal tract section are compressed between the first pressure area and the second pressure area such that the sum of the first pressure area and the second pressure area increases during the compression to seal the first gastro-intestinal tract section and the second gastro-intestinal tract section;
 wherein the first body and/or the second body are further configured such that, during use, the sum of the first pressure area and the second pressure area increases in the direction of the cutting section of said gastro-intestinal tract sections.

2. The surgical instrument according to claim 1, wherein the first body and/or the second body comprise a swellable hydrogel.

3. The surgical instrument according to claim 2, wherein the hydrogel is configured to be placed where the first gastro-intestinal tract section and the second gastro-intestinal tract section are compressed such that the hydrogel on swelling is configured to exert a force that seals said gastro-intestinal tract sections.

4. The surgical instrument according to claim 3, wherein the hydrogel is placed such that the hydrogel on swelling is configured to result in additional contact between submucosal layers of both the first gastro-intestinal tract section and the second gastro-intestinal tract section without compromising vascularization of these additionally contacted submucosal layers to promote healing by primary intent.

5. The surgical instrument according to claim 2, wherein the hydrogel is capable of swelling in an amount selected from the group consisting of 0-100 vol %, 10-80 vol %, and about 50 vol % with respect to the original volume of the hydrogel.

6. The surgical instrument according to claim 2, wherein the hydrogel comprises one or more antibiotics.

7. The surgical instrument according to claim 6, further comprising a cover on at least part of a surface of the hydrogel that is configured to not contact said gastro-intestinal tract sections, such that the antibiotics are delivered to said sealed gastro-intestinal tract sections.

8. The surgical instrument according to claim 6, further comprising a cover on the entire surface of the hydrogel that is configured to not contact said gastro-intestinal tract sections, such that the antibiotics are delivered to said sealed gastro-intestinal tract sections.

9. The surgical instrument according to claim 1, wherein the first body and/or the second body are configured to compress the first gastro-intestinal tract section and the second gastro-intestinal tract section between an inclined first pressure area and/or an inclined second pressure area.

10. The surgical instrument according to claim 1, which is a surgical stapler comprising an anvil and a casing, wherein the first body comprises the anvil and the second body comprises the casing, wherein the casing comprises a staple cartridge and a stapler base through which staples can be driven against the anvil.

11. The surgical instrument according to claim 10, wherein the anvil comprises an inner anvil part having an inner anvil pressure area and an outer anvil part having an outer anvil pressure area, wherein the inner anvil pressure area and the outer anvil pressure area comprise the first pressure area, wherein the inner anvil part is configured to be independently movable from the outer anvil part such that the first gastro-intestinal tract section and the second gastro-intestinal tract section can be compressed initially between the outer anvil pressure area and at least part of the second pressure area then subsequently further compressed between the inner anvil pressure area and at least part of the second pressure area.

12. The surgical instrument according to claim 10, wherein the stapler base comprises an inner stapler base part having an inner stapler base pressure area and an outer stapler base part having an outer stapler base pressure area, wherein the inner stapler base pressure area and the outer stapler base pressure area are part of the second pressure area,
wherein the inner stapler base part is configured to be independently movable from the outer stapler base part such that the first gastro-intestinal tract section and the second gastro-intestinal tract section are initially compressed between the outer stapler base pressure area and at least part of the first pressure area then subsequently further compressed between the inner stapler base pressure area and at least part of the first pressure area.

13. The surgical instrument according to claim 1, wherein the surgical stapler is a surgical circular stapler or a surgical linear stapler.

14. A surgical instrument for performing anastomosis of a first gastro-intestinal tract section and a second gastro-intestinal tract section, said instrument comprising:
a first body having a first pressure area;
a second body having a second pressure area;
connection means connecting the first body and the second body, wherein the connection means is configured to move the first body between an open position away from the second body and a closed position near the second body;
wherein the first body and the second body are configured such that, during use, the first gastro-intestinal tract section and the second gastro-intestinal tract section are compressed between the first pressure area and the second pressure area such that the sum of the first pressure area and the second pressure area increases during the compression to seal the first gastro-intestinal tract section and the second gastro-intestinal tract section;
wherein the first body and/or the second body are further configured such that, during use, the sum of the first pressure area and the second pressure area increases in the direction of said gastro-intestinal tract sections' lumen.

15. A surgical instrument for performing anastomosis of a first gastro-intestinal tract section and a second gastro-intestinal tract section, said instrument comprising:
a first body having a first pressure area;
a second body having a second pressure area;
connection means connecting the first body and the second body, wherein the connection means is configured to move the first body between an open position away from the second body and a closed position near the second body;
wherein the first body and the second body are configured such that, during use, the first gastro-intestinal tract section and the second gastro-intestinal tract section are compressed between the first pressure area and the second pressure area such that the sum of the first pressure area and the second pressure area increases during the compression to seal the first gastro-intestinal tract section and the second gastro-intestinal tract section and such that, during the compression, muscularis and/or mucosal layers are crushed or stripped from submucosal layers of the first gastro-intestinal tract section and the second gastro-intestinal tract section such that said submucosal layers contact each other.

* * * * *